United States Patent [19]

Couch

[11] Patent Number: 5,657,367
[45] Date of Patent: Aug. 12, 1997

[54] LATERAL DECUBITUS PATIENT POSITIONING DEVICE

[76] Inventor: Denver Couch, 5728 Imperial Key, Tampa, Fla. 33615

[21] Appl. No.: 671,397

[22] Filed: Jun. 26, 1996

[51] Int. Cl.[6] .................................................. G03B 42/02
[52] U.S. Cl. ........................ 378/177; 378/167; 378/180
[58] Field of Search ............................... 378/167, 172, 378/174, 177, 178, 180, 173

[56] References Cited

U.S. PATENT DOCUMENTS

| | | | |
|---|---|---|---|
| 3,916,207 | 10/1975 | Reed | 378/177 |
| 4,414,683 | 11/1983 | Robinson | 378/177 |
| 5,450,462 | 9/1995 | Tanaka | 378/167 |

Primary Examiner—Don Wong

[57] ABSTRACT

A patient positioning device (FIG. 1a) made of a sheet of rigid material having a back (10) and a base (12) at right angles to one another, and of sufficient size to support a patient (24) (FIG. 2a) during movement into a lateral decubitus position. A pad (14) is placed upon the top surface of the base (12) of sufficient size to provide comfort and elevation to the patient (24). The pad (14) is placed at a certain distance from the back (10) to create a slot (16) to accommodate a film cassette (28) parallel to the back (10). The patient (24) is supported on an even plane with the film cassette (28) between patient (24) and back (10) when in a proper lateral decubitus position (FIG. 2e).

1 Claim, 2 Drawing Sheets

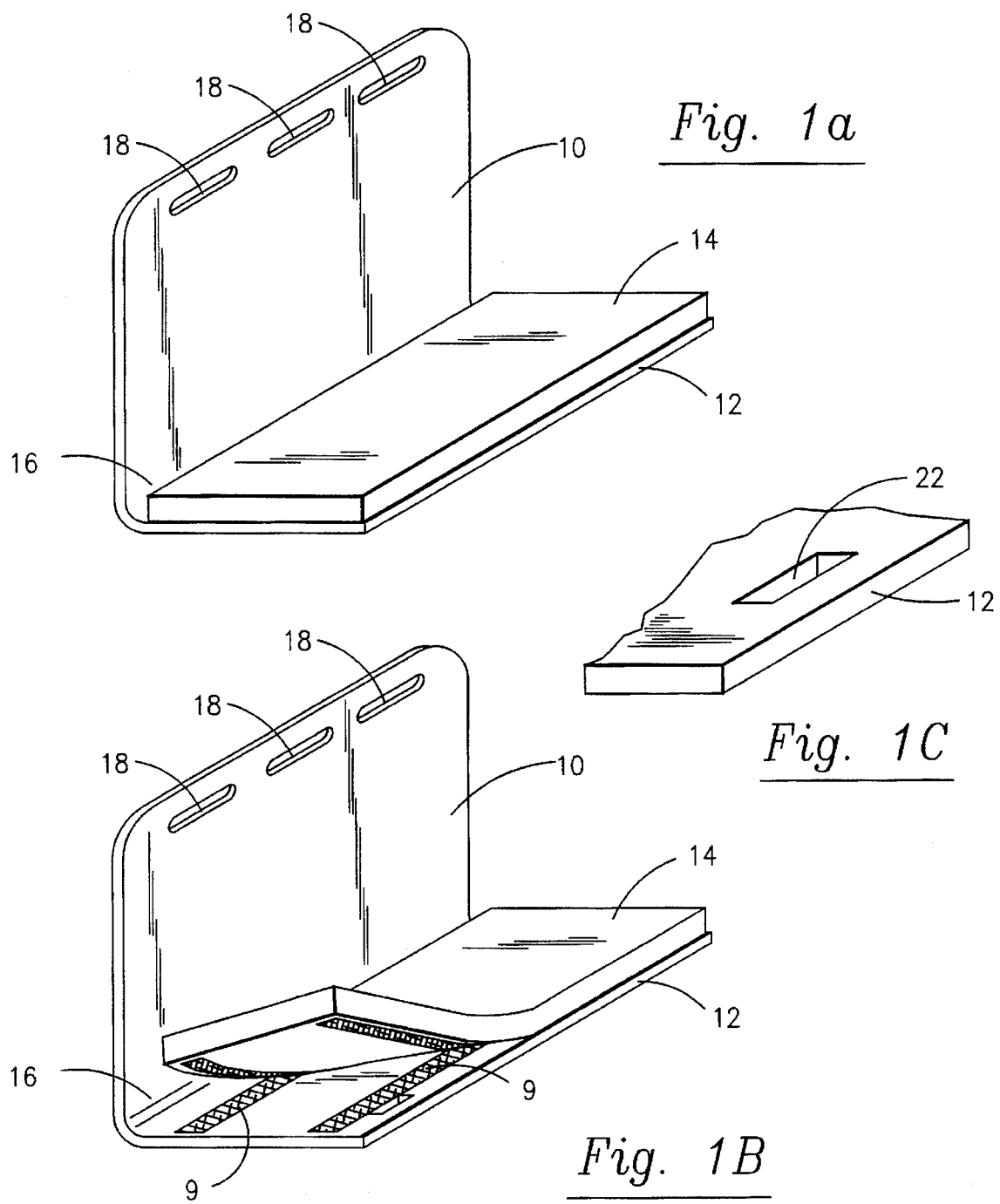

LATERAL DECUBITUS PATIENT POSITIONING DEVICE

BACKGROUND—FIELD OF INVENTION

This invention relates to radiography, specifically to a new device for placing a patient in a lateral decubitus position to facilitate a radiographic procedure.

BACKGROUND—DESCRIPTION OF PRIOR ART

A decubitus procedure requires that a patient be lying down with the x-ray beam parallel to the horizon. Heretofore the placement of a patient into a lateral decubitus position involved turning a patient by hand. Depending upon the patient's size and condition this often required more than one person to accomplish. Moreover, certain lateral decubitus procedures require that the patient be elevated so that the film cassette can be placed slightly lower than the patient in order to include the entire area of interest on the radiograph. This necessitated rolling the patient upon his or her side onto a stack of sheets or towels, or upon a sponge. This method usually added to the patient's discomfort and to the stress of the x-ray technologist. Performing this procedure at a patient's bedside created even more problem.

When a patient is unable to come to the radiology department for a procedure, he or she will likely be incapacitated and unable to assist the technologist during positioning. Since hospital beds are designed to meet the needs of the patient, the mattresses may be composed of fluid, sand, air, water, etc. These situations add to the difficulty of positioning a patient since these surfaces are often soft and uneven. It becomes nearly impossible to place and maintain a patient and film cassette on an even plane. This sometimes requires that one person hold the patient and film cassette while another takes the x-ray. Obviously these methods present a number of disadvantages:

(a) Increased patient discomfort;
(b) Repeat x-rays due to poor positioning;
(c) Increased radiation exposure to all concerned because of repeat x-rays;
(d) Extra person(s) often needed to hold patient and/or film cassette in position;
(e) Needless radiation exposure to person(s) holding patient and film cassette.

Objects and Advantages

Accordingly, several objects and advantages of the lateral decubitus positioning device are:

(a) Patient is made more comfortable by being supported throughout the procedure with the positioning device.
(b) Patient and film cassette are maintained in the proper position, on an even plane thereby virtually eliminating the need for repeating the procedure;
(c) Reduced radiation exposure to persons involved in the procedure since repeat x-rays are seldom necessary;
(d) Eliminates the need for extra person(s) to hold the patient and/or film cassette in position;
(e) Eliminates radiation exposure to extra person(s) since none will be needed to assist in the procedure.

Further objects and advantages of my lateral decubitus positioning device will become apparent from a consideration of the drawings and the ensuing description.

DRAWING FIGURES

FIG. 1a shows a perspective of the lateral decubitus patient positioning device.

FIG. 1b shows the removable pad and a typical method of attachment

FIG. 1c shows an exploded view of a corner of the positioning device indicating an opening for strapping material.

Figure 2A:
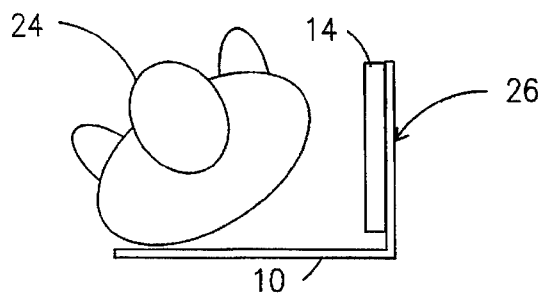
FIGS. 2a to 2e show the method of operation of the positioning device.

REFERENCE NUMERALS IN DRAWINGS 10 back of positioning device
12 base of positioning device
14 pad
16 slot for film cassette
18 opening for hand hold
20 typical fastening material for pad
22 opening for strapping material located on each corner of base
24 patient
26 positioning device
28 film cassette Description—FIGS. 1a to 1c A typical embodiment of the decubitus patient positioning device is illustrated in FIGS. 1a to 1c. The device is formed from a sheet of rigid material into aback 10 and a base 12 at right angles to one another. A removable pad 14 is attached to the top of the base 12. The pad 14 is made of a certain size, and attached in such a way as to create a film cassette slot 16 between pad 14 and back 10. FIG. 1b shows a typical method of fastening pad 14 to back 10 using a book-and-loop material. Openings are located near the top edge of back 10 to provide hand holds 18. Openings are also located near the outside edge of base 12 to provide strap slots 22 (FIG. 1c) for patient strapping material.

Operation—FIGS. 1a to 2e

The manner of using the lateral decubitus patient positioning device is as follows:

FIG. 2a Roll patient 24 up from supine position and place back 10 underneath patient 24 with base 12 nearest the side of patient 24 that is to be down when positioning is completed.

Figure 2B:
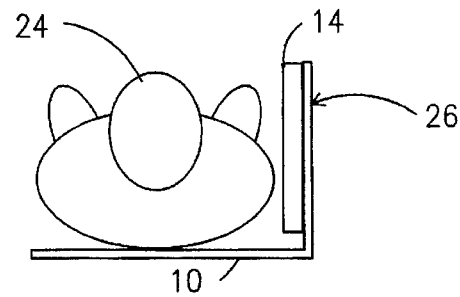

FIG. 2b Roll patient 24 onto his or her back with side to be down against pad 14

Figure 2C:
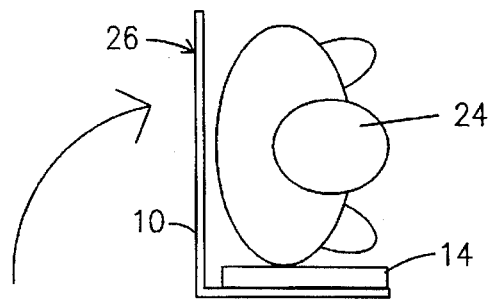

FIG. 2c Firmly grasp hand holds 18 and turn the positioning device with patient 24 up into a lateral decubitus position.

Figure 2D:
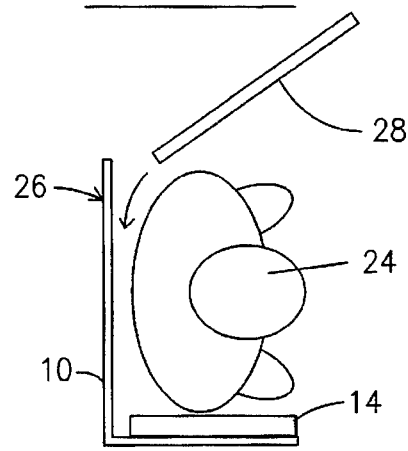
Figure 2E:
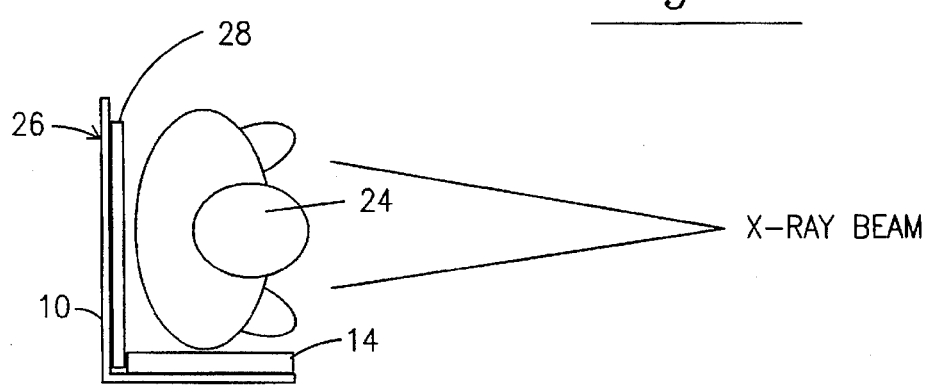

FIG. 2d Place fill cassette 26 between patient 24 and back 10 into film cassette slot 16 (FIG. 2e).

FIG. 2e Perform x-my procedure and reverse the aforementioned steps to remove the positioning device.

Summary, Ramifications, and Scope

Accordingly, the reader will see that the decubitus patient positioning device of this invention can be used to position a patient easily and efficiently with minimal stress to both patient and person performing the procedure. Moreover, this invention will reduce radiation exposure to all concerned by virtually eliminating the need for repeat x-rays due to improper positioning.

While my above description contains many specificities, these should not be construed as limitations on the scope of the invention, but rather as an exemplification of one preferred embodiment thereof. Many other variations are possible. For example any decubitus examination can be performed by using this device to hold the film cassette and the patient in a proper position, e.g. cross-table spine, head, neck, chest, abdomen, pelvis, extremities, etc. Accordingly, the scope of the invention should be determined not by the embodiment illustrated, but by the appended claims and their legal equivalents.

I claim:

1. A patient positioning device designed to support and secure a patient and film cassette during the movement and placement of said patient into a lateral decubitus position to facilitate a cross-table radiographic procedure, comprising:

(a) a sheet of rigid material formed into a back and a base at right angles to one another of sufficient size to support said patient during the movement and placement of said patient into a decubitus position (b) a pad placed upon the top side of said base of sufficient size to support and elevate said patient (c) a film cassette slot formed by placement of said pad at a certain distance from said back of sufficient size to hold said film cassette parallel to said back and a certain distance below said patient (d) openings in said back of sufficient number, size and placement to create hand holds to facilitate lifting and positioning of said patient (e) openings in said base of sufficient size and placement to create strap slots as a means to secure said patient when necessary.

* * * * *